United States Patent
Stainsby et al.

(10) Patent No.: US 11,707,204 B2
(45) Date of Patent: Jul. 25, 2023

(54) METHOD, SYSTEM AND APPARATUS FOR IMAGE-GUIDED INSERTION OF IMPLANT DEVICES

(71) Applicant: SYNAPTIVE MEDICAL INC., Toronto (CA)

(72) Inventors: Jeff Stainsby, Toronto (CA); Alexander Gyles Panther, Toronto (CA); Chad Tyler Harris, Toronto (CA); Cameron Anthony Piron, Toronto (CA)

(73) Assignee: Synaptive Medical Inc.

( * ) Notice: Subject to any disclaimer, the term of this patent is extended or adjusted under 35 U.S.C. 154(b) by 323 days.

(21) Appl. No.: 15/762,853

(22) PCT Filed: Oct. 6, 2015

(86) PCT No.: PCT/IB2015/057643
§ 371 (c)(1),
(2) Date: Mar. 23, 2018

(87) PCT Pub. No.: WO2017/060753
PCT Pub. Date: Apr. 13, 2017

(65) Prior Publication Data
US 2018/0279904 A1    Oct. 4, 2018

(51) Int. Cl.
*A61B 5/055* (2006.01)
*G01R 33/50* (2006.01)
(Continued)

(52) U.S. Cl.
CPC .............. *A61B 5/055* (2013.01); *G01R 33/50* (2013.01); *G01R 33/5608* (2013.01);
(Continued)

(58) Field of Classification Search
None
See application file for complete search history.

(56) References Cited

U.S. PATENT DOCUMENTS

| 8,482,279 | B2 | 7/2013 | Chen et al. |
| 8,837,860 | B1 * | 9/2014 | Grady ................... G06T 11/005 600/458 |

(Continued)

FOREIGN PATENT DOCUMENTS

| WO | 2005101045 A1 | 10/2005 |
| WO | WO-2005101045 A1 * | 10/2005 ........... G01R 33/285 |

(Continued)

OTHER PUBLICATIONS

Hinks, R.S., Bronskill, M.J., Kucharczyk, W., Bernstein, M., Collick, B.D. and Henkelman, R.M., 1998. Invited "MR systems for image-guided therapy." Journal of Magnetic Resonance Imaging, 8( I ), pp. I9-25., MEDLINE, EBSCOhost, viewed May 4, 2016.

(Continued)

*Primary Examiner* — Bill Thomson
*Assistant Examiner* — Aminah Asghar

(57) ABSTRACT

A method of imaging an implant device in a computing device is provided. The computing device includes a processor interconnected with a memory and a display. The method includes, at the processor: obtaining a first magnetic resonance (MR) image of a patient tissue, the first MR image containing a first magnetic field strength indicator; responsive to the implant device being inserted in the patient tissue, obtaining a second MR image of the patient tissue, the second MR image containing a second magnetic field strength indicator smaller than the first magnetic field strength indicator; registering the second MR image with the first MR image; generating a composite image from the first MR image and the second MR image; and presenting the composite image on the display.

18 Claims, 7 Drawing Sheets

(51) Int. Cl.
*G01R 33/56* (2006.01)
*A61N 1/05* (2006.01)
*G01R 33/563* (2006.01)
*A61B 34/20* (2016.01)

(52) U.S. Cl.
CPC ........ *G01R 33/56341* (2013.01); *A61B 34/20* (2016.02); *A61N 1/0534* (2013.01)

(56) References Cited

U.S. PATENT DOCUMENTS

| | | | | |
|---|---|---|---|---|
| 2003/0214290 | A1* | 11/2003 | van Muiswinkel | G06T 5/50 324/307 |
| 2008/0226149 | A1* | 9/2008 | Wischmann | G06T 11/005 382/131 |
| 2013/0085362 | A1 | 4/2013 | Choi et al. | |
| 2013/0230224 | A1* | 9/2013 | Claude | A61B 5/055 382/131 |
| 2014/0079303 | A1* | 3/2014 | Pfrengle | G06T 7/254 382/128 |
| 2014/0161338 | A1* | 6/2014 | Machado | G06T 7/344 382/131 |
| 2014/0292325 | A1* | 10/2014 | Heule | G01R 33/448 324/309 |
| 2014/0303486 | A1* | 10/2014 | Baumgartner | A61B 34/20 600/414 |
| 2015/0010223 | A1* | 1/2015 | Sapiro | A61B 6/501 382/131 |
| 2015/0073267 | A1* | 3/2015 | Brannan | A61B 8/12 600/424 |
| 2015/0160322 | A1* | 6/2015 | Matthews | G01R 33/56341 324/322 |
| 2016/0033602 | A1* | 2/2016 | Fritz | G01R 33/4816 324/309 |
| 2016/0120457 | A1* | 5/2016 | Wu | A61B 5/4836 600/411 |
| 2016/0171157 | A1* | 6/2016 | Mielekamp | G16H 30/20 345/589 |
| 2016/0310761 | A1* | 10/2016 | Li | G06K 9/52 |
| 2016/0345834 | A1* | 12/2016 | Hasan | A61B 1/00009 |
| 2017/0209071 | A1* | 7/2017 | Zhao | G06T 7/149 |
| 2018/0114087 | A1* | 4/2018 | Kamen | G06T 7/0012 |

FOREIGN PATENT DOCUMENTS

| | | |
|---|---|---|
| WO | 2011063517 A1 | 6/2011 |
| WO | 2014025886 A1 | 2/2014 |
| WO | 2014138914 A1 | 9/2014 |
| WO | 2014138997 A1 | 9/2014 |
| WO | 2014139024 A1 | 9/2014 |
| WO | WO-2014138997 A1 * | 9/2014 |
| WO | WO-2014139022 A1 | 9/2014 |
| WO | 2014186715 A1 | 11/2014 |
| WO | WO-2014194006 A1 | 12/2014 |
| WO | 2016041047 A1 | 3/2016 |
| WO | 2016042351 A1 | 3/2016 |

OTHER PUBLICATIONS

Karamitsos, T.D., Francis, J.M., Myerson, S., Selvanayagam, J.B. and Neubauer, S., 2009. "The role of cardiovascular magnetic resonance imaging in heart failure." Journal of the American College of Cardiology, 54(15), pp. 1407-1424. Retrieved from: htto://content.onlinejacc.org/article.aspx?articleid= 1140100#tab 1.

Zhou, H., Hernandez, C., Goss, M., Gawlik, A. and Exner, A.A, 2014. "Biomedical Imaging in Implantable Drug Delivery Systems." Current drug targets, 16(6), pp. 672-682. Retrieved from htto://www. ncbi.nlm.nih.gov/pmc/articles/PMC44415941.

International Preliminary Report on Patentability, dated Jan. 19, 2018, by IPEA/CA, re PCT International Patent Application No. PCT/IB2015/057643.

International Search Report dated May 24, 2016 for International Application No. PCT/IB2015/057643.

Written Opinion dated May 24, 2016 for International Application No. PCT/IB2015/057643.

CIPO, Examination Report, dated Feb. 1, 2019, re Canadian Patent Application No. 2999804.

CIPO, Examination Report, dated Mar. 5, 2020, re Canadian Patent Application No. 2999804.

* cited by examiner

METHOD, SYSTEM AND APPARATUS FOR IMAGE-GUIDED INSERTION OF IMPLANT DEVICES

FIELD

The specification relates generally to image-based medical guidance systems, and specifically to a method, system and apparatus for image-guided insertion of implant devices.

BACKGROUND

Certain medical devices are employed by implantation into patient tissue. An examples of such devices is a deep brain stimulation (DBS) probe, which is inserted into a patient's brain to deliver electrical pulses to selected anatomical structures. The nature of the insertion prevents the surgeon from directly viewing the position of the electrodes, and conventional DBS probe insertion procedures therefore rely on medical imaging to confirm that the probe is correctly placed.

The anatomical structures that are relevant to such devices can be small. For example, DBS probes are often inserted adjacent to the sub-thalamic nucleus (STN) in the brain. Viewing such structures can be accomplished with various imaging modalities, including MRI. Higher magnetic field strengths (e.g. 3T and above) are particularly effective for imaging structures such as the STN. However, the electrodes of DBS probes and similar components of other implants can interfere with MR imaging, particularly at higher field strengths, producing artifacts and distortions that render confirmation of the probe's position difficult or impossible.

SUMMARY

According to an aspect of the specification, a method of imaging an implant device is provided in a computing device having a processor interconnected with a memory and a display. The method comprises, at the processor: obtaining a first magnetic resonance (MR) image of a patient tissue, the first MR image containing a first magnetic field strength indicator; responsive to the implant device being inserted in the patient tissue, obtaining a second MR image of the patient tissue, the second MR image containing a second magnetic field strength indicator smaller than the first magnetic field strength indicator; registering the second MR image with the first MR image; generating a composite image from the first MR image and the second MR image; and presenting the composite image on the display.

According to a further aspect of the specification, a computing device is provided for imaging an implant device, comprising: a memory; a display; and a processor interconnected with the memory and the display, the processor configured to perform the above method.

BRIEF DESCRIPTIONS OF THE DRAWINGS

Embodiments are described with reference to the following figures, in which.

DETAILED DESCRIPTION OF THE EMBODIMENTS

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

Unless defined otherwise, all technical and scientific terms used herein are intended to have the same meaning as commonly understood to one of ordinary skill in the art. Unless otherwise indicated, as used herein, the following terms are intended to have the following meanings:

As used herein the term "intraoperative" refers to an action, process, method, event or step that occurs or is carried out during at least a portion of a medical procedure. The term "preoperative" as used herein refers to an action, process, method, event or step that occurs or is carried out before the medical procedure begins. The terms intraoperative and preoperative, as defined herein, are not limited to surgical procedures, and may refer to other types of medical procedures, such as diagnostic and therapeutic procedures.

Figure 1:
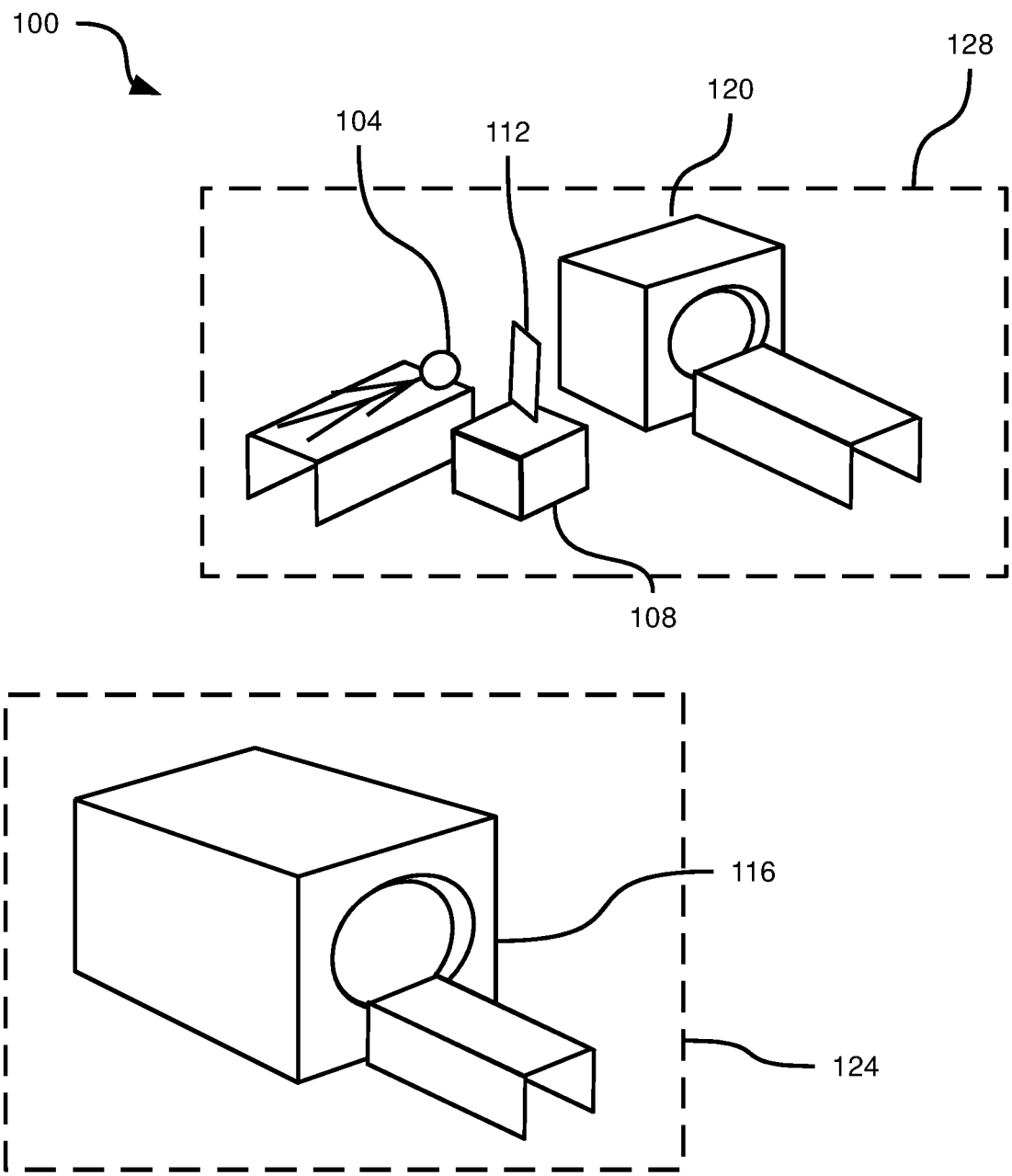
FIG. 1 depicts a system for image-guided insertion of implant devices, according to a non-limiting embodiment.

FIG. 1 depicts a system 100 for image-guided insertion of implant devices. System 100, as will be discussed in greater detail below, is configured to generate one or more guidance images for use intraoperatively or postoperatively in connection with a procedure to insert an implant device (not shown) into a tissue of a patient 104. The implant device, in general, is a device that, during insertion into patient 104 may not be directly (i.e. optically) visible to the medical staff (e.g. surgeon) performing the insertion.

An examples of such a device is a deep brain stimulation (DBS) probe. DBS probes generally include an array of electrodes (e.g. in a linear arrangement along the length of the probe), and are commonly inserted through an opening in the skull of patient 104. Following entry through the skull, the probe is inserted through the tissue of the brain until the electrodes of the probe are adjacent to a target structure within the brain (e.g. the sub-thalamic nucleus (STN)). However, the surgeon may have limited visibility, or no visibility, of the position of the electrodes relative to the STN from the opening in the skull of patient 104.

Another example of an implant device as discussed herein is a cochlear implant. As with a DBS probe, the desired insertion location of a cochlear implant electrode is adjacent to structures within patient 104 (e.g. the cochlea) that are not directly visible to the surgeon inserting the implant.

Various components of system 100 interact to generate the above-mentioned guidance images. In particular, system 100 includes a computing device 108 connected to a display 112. Computing device 108 is configured to generate the guidance images, and can control display 112 to present those images. Computing device 108 generates the guidance images based on initial images obtained from at least one imaging device. In general, the initial images on which computing device 108 operates to generate the guidance images are captured using the same imaging modality. In the present example, that imaging modality is magnetic resonance imaging (MRI). In other embodiments, however, the techniques described herein may be applied to other imaging modalities.

The above-mentioned imaging device is therefore, in the present example, an MRI scanner. More specifically, the initial images on which computing device 108 operates to generate the guidance images include images acquired at different magnetic field strengths. System 100 therefore includes a first MRI scanner 116, and a second MRI scanner 120. MRI scanner 116 has a greater field strength than MRI scanner 120. For example, MRI scanner 116 can have a field strength of 7 T, while scanner 116 can have a field strength of 0.5 T. A wide variety of other field strengths are also contemplated. For instance, scanner 116 can have a field strength of 3 T while scanner 120 can have a field strength of 1 T. As a further example, scanner 116 can have a field strength of 3 T while scanner 120 can have a field strength of 0.3 T.

As illustrated in FIG. 1, scanners 116 and 120 can be installed in different areas 124 and 128, respectively, of a building (or in separate buildings). In some embodiments, scanner 120 can be installed within an operating theatre for use in capturing intraoperative images. In other embodiments, however, scanner 120 can be located outside the operating theatre, or in the same building or room as scanner 116.

Computing device 108, as will be described in greater detail below, is configured to obtain images captured using scanners 116 and 120, and to perform various processing actions to generate guidance images for presentation on display 112. Before a detailed discussion of the above-mentioned functionality of computing device 108, a description of the components of computing device 108 will be provided.

Figure 2:
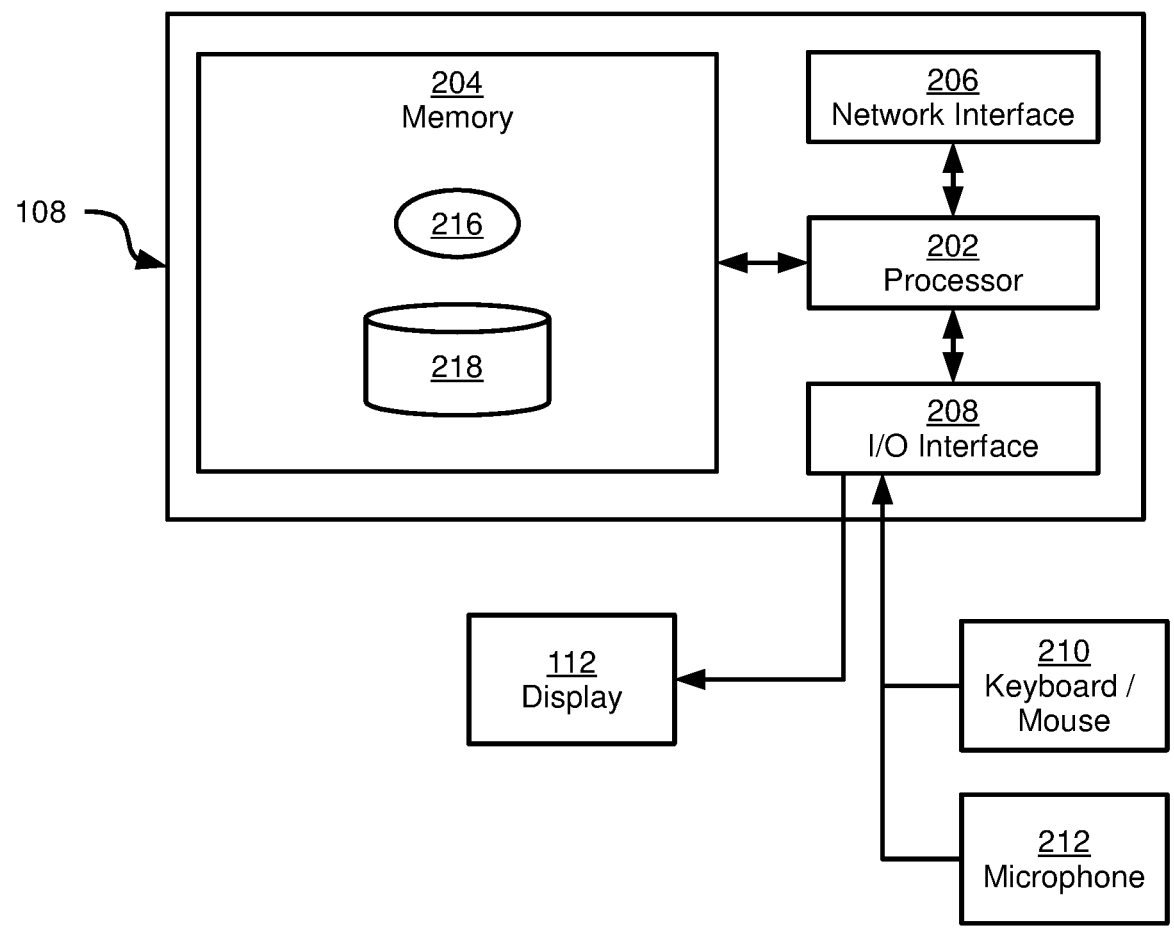
FIG. 2 depicts certain internal components of the computing device of the system of FIG. 1, according to a non-limiting embodiment.

Referring to FIG. 2, certain internal components of computing device 108 are depicted, including a central processing unit (also referred to as a microprocessor or simply a processor) 202 interconnected with a non-transitory computer readable storage medium such as a memory 204.

Processor 202 and memory 204 are generally comprised of one or more integrated circuits (ICs), and can have a variety of structures, as will now occur to those skilled in the art (for example, more than one CPU can be provided). Memory 204 can be any suitable combination of volatile (e.g. Random Access Memory ("RAM")) and non-volatile (e.g. read only memory ("ROM"), Electrically Erasable Programmable Read Only Memory ("EEPROM"), flash memory, magnetic computer storage device, or optical disc) memory. In the present example, memory 204 includes both a volatile memory and a non-volatile memory. Other types of non-transitory computer readable storage medium are also contemplated, such as compact discs (CD-ROM, CD-RW) and digital video discs (DVD).

Computing device 108 can also include a network interface 206 interconnected with processor 202. Network interface 206 allows computing device 108 to communicate with other devices via a network (e.g. a local area network (LAN), a wide area network (WAN) or any suitable combination thereof). Network interface 206 thus includes any necessary hardware for communicating over such networks, such as radios, network interface controllers (NICs) and the like. The devices with which computing device 108 can communicate are not particularly limited in nature, and can include other computing devices, scanners 116 and 120, and the like.

Computing device 108 can also include an input/output interface 208, including the necessary hardware for interconnecting processor 202 with various input and output devices. Interface 208 can include, among other components, a Universal Serial Bus (USB) port, an audio port for sending and receiving audio data, a Video Graphics Array (VGA), Digital Visual Interface (DVI) or other port for sending and receiving display data, and any other suitable components.

Via interface 208, computing device 108 is connected to input devices including a keyboard and mouse 210, a microphone 212, as well as output devices, including display 112. Computing device 108 can also be connected to devices such as a tracking system (e.g. an infrared-based optical tracking system), imaging scopes, lighting systems and the like. Those components, however, are not directly relevant to the present discussion and are therefore not illustrated. Other input (e.g. touch screens) and output devices (e.g. speakers) will also occur to those skilled in the art.

It is contemplated that I/O interface 208 may be omitted entirely in some embodiments, or may be used to connect to only a subset of the devices mentioned above. The remaining devices may be connected to computing device 108 via network interface 206.

Computing device 108 stores, in memory 204, an image processing application 216 (also referred to herein as application 216) comprising a plurality of computer readable instructions executable by processor 202. When processor 202 executes the instructions of application 216 (or, indeed, any other application stored in memory 204), processor 202 performs various functions implemented by those instructions, as will be discussed below. Processor 202, or computing device 108 more generally, is therefore said to be "configured" or "operating" to perform those functions via the execution of application 216.

Also stored in memory 204 are various data repositories, including a patient data repository 218. Patient data repository 218 can contain a surgical plan defining the various steps of a surgical procedure to be conducted on patient 104 (such as the implantation of a DBS probe), as well as image data relating to patient 104, such as initial images captured using scanners 116 and 120, as well as guidance images generated by computing device 108 based on those initial images.

As mentioned above, computing device 108 is configured, via the execution of application 216 by processor 202, to generate guidance images based on images obtained from scanners 116 and 120, for use in the insertion of implant devices (such as DBS probes or cochlear implants) into tissues of patient 104. The actions performed by computing device 108 to generate such images will be described in detail below.

Figure 3:
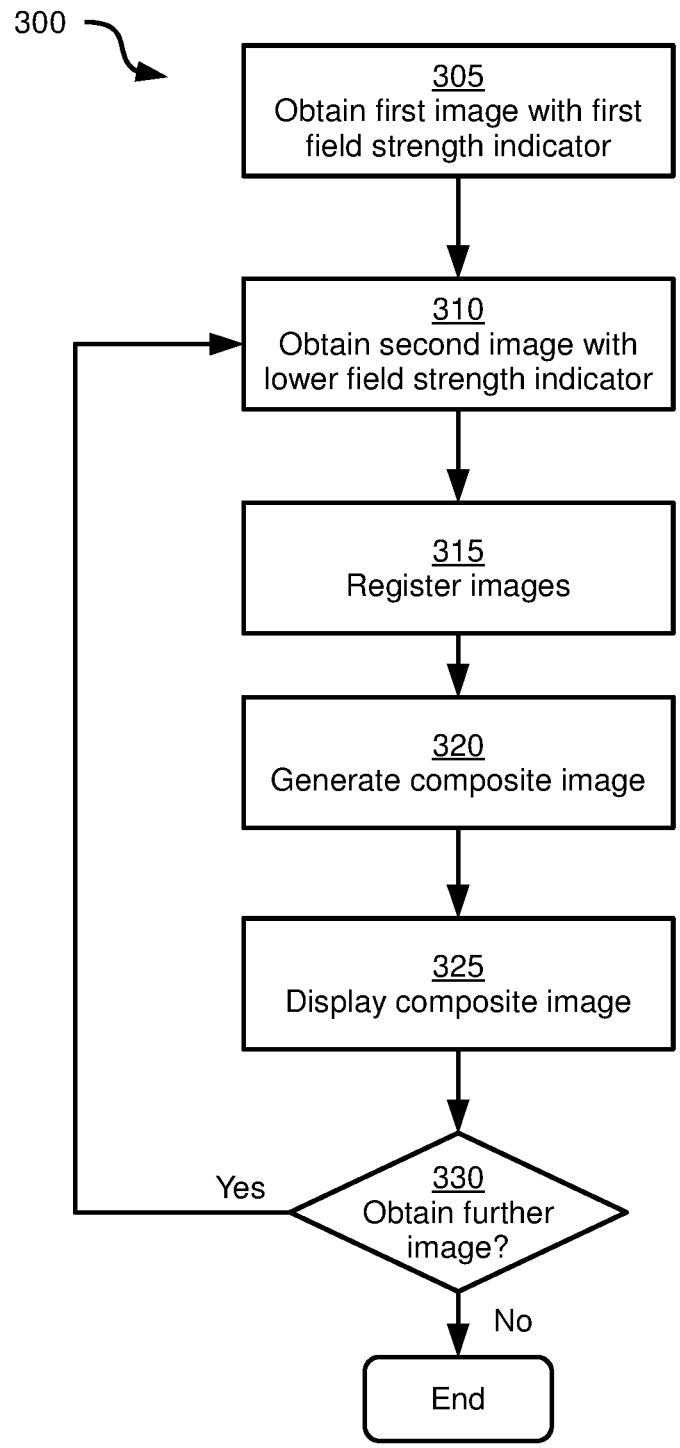
FIG. 3 depicts a method of generating guidance images for implant device insertion, according to a non-limiting embodiment.

Turning to FIG. 3, a method 300 of generating guidance images for implant device insertion is illustrated. Method 300 will be described in conjunction with its performance in system 100. The blocks of method 300, as described below, are performed by computing device 108, and more specifically, by processor 202 via the execution of application 216. In other embodiments, method 300 can be performed within other suitable systems.

At block 305, computing device 108 is configured to obtain a first image—in the present embodiment, a first MR image of a tissue of patient 104—containing a first magnetic field strength indicator. As will be apparent to those skilled in the art, images acquired with scanners 116 and 120 can include metadata, such as Digital Imaging and Communications in Medicine (DICOM) data specifying various imaging parameters. The field strength indicator contained in the first image indicates the strength of the magnetic field emitted by the scanner used to acquire that image.

The first image obtained at block 305 can be obtained via retrieval from memory 204 (e.g. from repository 218), having been captured at an earlier time via the control of scanner 116 by another computing device. In other embodiments, the first image can be obtained at block 305 directly from scanner 116. In other words, computing device 108 can be configured to control scanner 116 to capture the first image in some embodiments.

The first image is acquired prior to the insertion of the implant device, and is generally acquired preoperatively. The first image therefore depicts patient tissue, but does not depict any portion of the implant device. As noted above, the first image can be acquired using scanner 116, following which patient 104 may be transported to an operating theatre such as that contained in area 128 illustrated in FIG. 1.

At block 310, responsive to insertion (or at least partial insertion) of the implant device into the tissue of patient 104, computing device 108 is configured to obtain a second image—in the present embodiment, a second MR image—of the patient tissue. As with the first image, the second image can be obtained either directly from an imaging device under the control of computing device 108, or from memory 204 (having been stored in memory 204 previously) or from another computing device via network interface 206. The second MR image contains a second magnetic field strength indicator smaller than the first magnetic field strength indicator. In other words, the second image is acquired with a scanner having a lower field strength than the scanner with which the first image was acquired. In the present example, the first image can be acquired with scanner 116 (e.g. a 7 T scanner), while the second image can be acquired with scanner 120 (e.g. a 0.5 T scanner).

The second image is acquired either intraoperatively (i.e. during the procedure to insert the implant device into patient 104) or postoperatively (i.e. after the procedure is complete). More generally, the second image is acquired after the insertion of the implant device has begun, and thus the second image, as obtained by computing device 108, depicts at least a portion of the implant device.

Figure 4:
FIG. 4 depicts an example first image obtained during the performance of the method of FIG. 3, according to a non-limiting embodiment.
Figure 5:
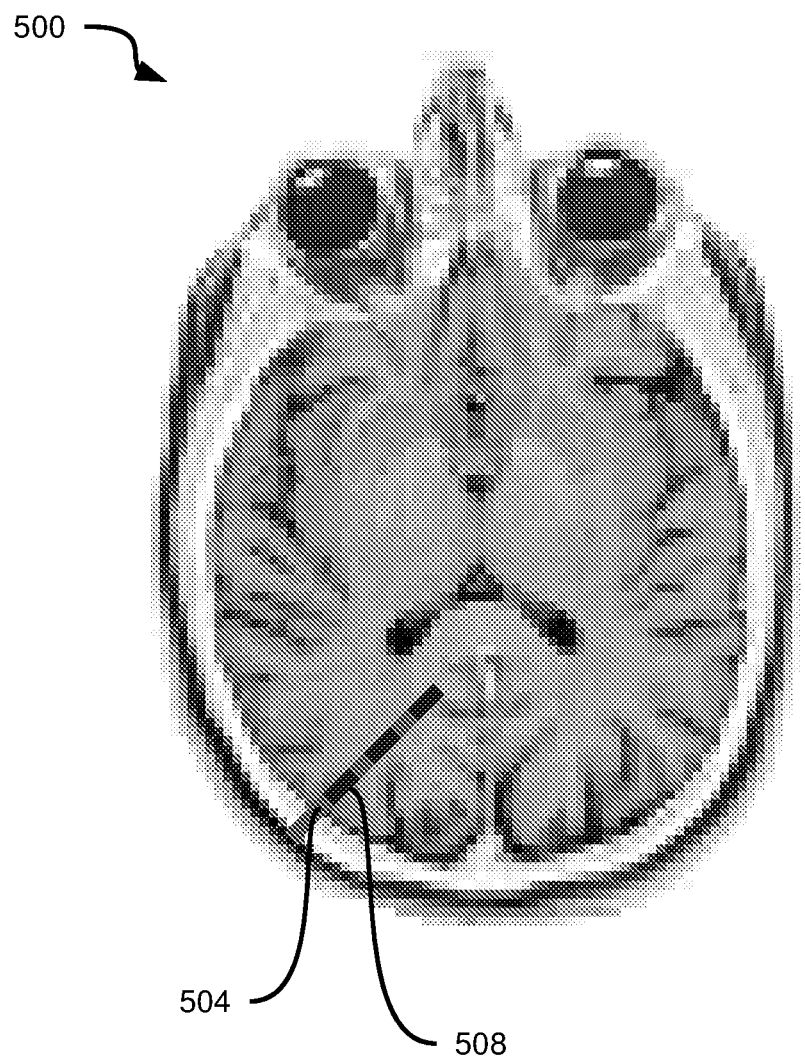
FIG. 5 depicts an example second image obtained during the performance of the method of FIG. 3, according to a non-limiting embodiment.

FIG. 4 depicts an example first image 400 of the brain of patient 104, as obtained at block 305. FIG. 5, meanwhile, depicts an example second image 500 of the brain of patient 104, as obtained at block 310. As seen by comparing images 400 and 500, image 400 depicts the patient tissue at a greater level of detail than image 500. This can arise because, for example, the higher field strength used to acquire first image 400 can provide a greater signal-to-noise ratio. The increased level of detail visible in first image 400 may also result from increased iron content in certain fine anatomical structures. For example, the STN can have an elevated iron content in comparison with surrounding issues, and thus is less suitable for imaging at lower magnetic field strengths (i.e. is less easily viewed in images such as image 500).

It will also be noted that image 500, although depicting patient tissue in less detail than image 400, depicts a portion of an implant device 504. In the present example, device 504 is a DBS probe including a plurality of electrodes 508. As noted earlier, imaging a device such as DBS probe 504 under a greater magnetic field such as that used to acquire image 400 can result in distortions and artifacts, up to and including complete signal loss in the region surrounding probe 504.

Images 400 and 500 can be acquired using any suitable MR protocol (e.g. gradient echo based sequences). In a preferred embodiment, images 400 and 500 are quantitative images, such as T1 maps or T2 maps, whose acquisition will be familiar to those skilled in the art. In a T1 map image, each pixel or voxel has a value that indicates the absolute spin-lattice relaxation time (T1) for the tissue depicted by that pixel or voxel. In a T2 map image, each pixel or voxel has a value that indicates the absolute spin-spin relaxation time (T2) for the tissue depicted by that pixel or voxel.

Returning to FIG. 3, having obtained the two images at block 305 and 310, computing device 108 is configured to register the images at block 315. Image registration refers to the process of placing both images in a common coordinate system, such that any given set of coordinates in the common system identifies portions of both images depicting the same area of patient 104. In general, each obtained image begins with an image-specific coordinate system. For example, a two-dimensional preoperative image may have a coordinate system in which the origin lies at the lower-left corner of the image. A two-dimensional intraoperative image may also have a coordinate system in which the origin lies at the lower-left corner of the image. However, because the two images may not depict exactly the same area of patient 104, the two coordinate systems cannot be directly compared. That is, the pixel located at (1200, 205) in image 400 may depict an entirely different portion of patient 104 than the pixel at (1200, 205) in image 500.

Therefore, in order to align images 400 and 500 on a common coordinate system, computing device 108 is configured to generate and apply a transformation operation is to at least one of the images. In the present example, it is contemplated that the transformation operation is to be applied to image 500, but the transformation operation can also be applied to image 400 in other embodiments. The nature of the transformation is not particularly limited, and a variety of image registration algorithms will occur to those skilled in the art for determining such transformation operations. In general, the transformation operation manipulates the pixels or voxels of one or both of the images (e.g. by translation, rotation, distortion, scaling, and the like) to place the pixels or voxels in the common coordinate system.

The transformation can be determined by computing device 108 by comparing images 400 and 500 and identifying common features between the images, such as edges, intensities, and other image features (including anatomical features such as sulci and ventricles). Transformation parameters (e.g. scaling, rotation, localized deformations and the like) can be optimized by computing device 108 according to conventional algorithms to place such features in alignment.

In embodiments in which images 400 and 500 are T1 maps or T2 maps, image registration at block 315 may be accelerated by permitting the use of mutual information based image registration processes, because both images contain absolute measurements that can be compared directly (rather than image attributes such as contrast or colour, which are not necessarily directly comparable). Examples of image registration algorithms applicable to quantitative images such as T1 and T2 maps include quasi-Newton algorithms, simultaneous perturbation algorithms, and the like.

Upon completion of block 315, any given coordinate set of image 400 depicts the same (or substantially the same) region of patient tissue as the same coordinate set in image 500. At block 320, computing device 108 is configured to generate a composite image from the registered first and second images 400 and 500. In general, the composite image depicts the implant device as shown in second image 500, and patient tissue as shown in first image 400. Therefore, computing device 108 is configured to generate the composite image by selecting a region of second image 500 depicting the implant device, and overlaying the selected region of second image 500 on first image 400.

The selection of a region of second image 500 for use in the composite image at block 320 can be performed in various ways. For example, computing device 108 can be configured to select, for use in the composite image, any pixel or voxel from second image 500 having a value (e.g. a T1 value) that is different from the value in image 400 for the same location by at least a predefined threshold. If the difference in pixel or voxel values between images 400 and 500 for a given pixel or voxel does not exceed the threshold, the pixel or voxel from image 400 is placed in the composite image instead of the pixel or voxel from image 500. In other words, regions of the two images having low levels of mutual information can be identified during image registration, and in the composite image, data from image 400 in those regions can be placed instead of data from image 500. In some embodiments, the above-mentioned threshold can be altered, for example via input data received from keyboard/mouse 210.

Figure 6:
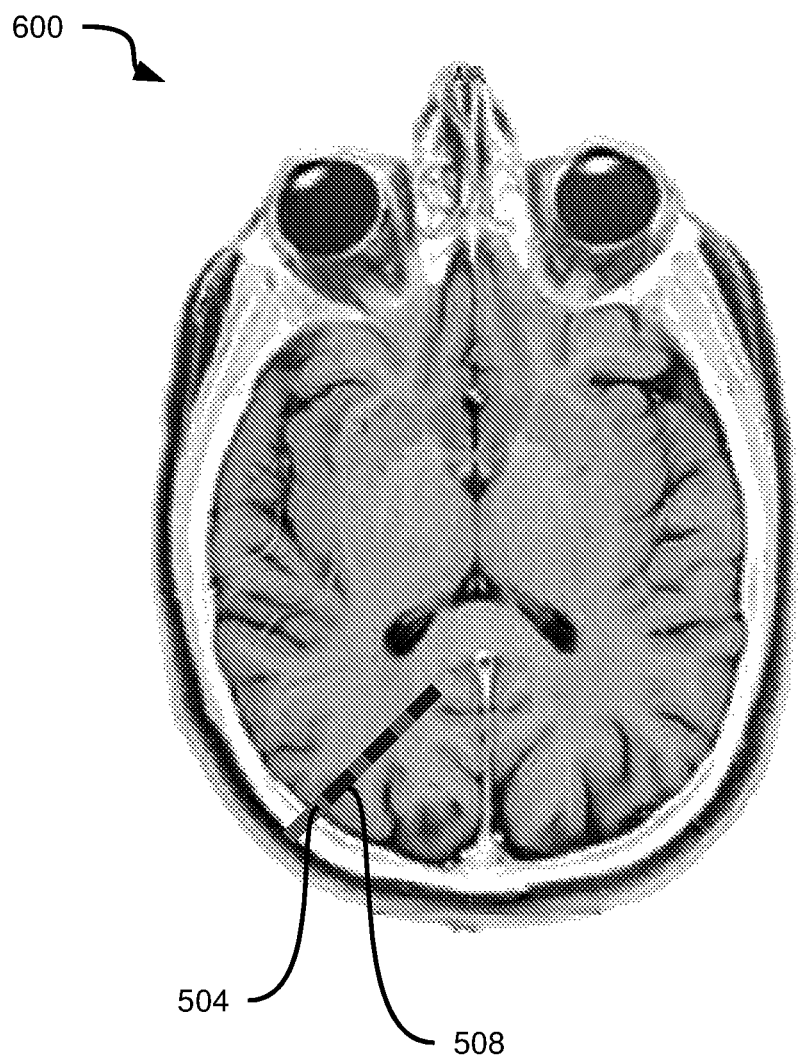
FIG. 6 depicts an example composite image generated during the performance of the method of FIG. 3, according to a non-limiting embodiment.

FIG. 6 illustrates a composite image 600 resulting from the performance of block 320. As seen in FIG. 6, probe 504 and electrodes 508 are visible in composite image 600; however, the remainder of image 600 contains data from image 400, and thus certain fine anatomical structures are visible to a greater degree in composite image 600 than in second image 500.

Referring again to FIG. 3, at block 325 computing device 108 is configured to present composite image 600 on display 112 (or any other suitable display connected to computing device 108). Following the performance of block 325, computing device 108 can be configured to determine whether to obtain a further intraoperative or postoperative image at block 330. For example, the determination at block 330 can include a determination as to whether input data has been received representing a command to obtain a further intraoperative or postoperative image. Such further images can be acquired following an intraoperative adjustment to the position of implant 504, or postoperatively to assess whether implant 504 has shifted within patient 104.

When the determination at block 330 is negative, the performance of method 300 ends. When, on the other hand, the determination at block 330 is affirmative, computing device 108 is configured to repeat the performance of blocks 310 to 325 to acquire a third image (e.g. a third MR image having a lower field strength indicator than first image 400), register the third image with first image 400, and generate a further composite image based on first image 400 and the third image. The third image can have the same field strength indicator as second image 500 (that is, the third image has a field strength indicator equal to the field strength indicator of second image 500), although this is not mandatory—the third image can be acquired using a different scanner than second image 500, and thus can be acquired at a different field strength, so long as the field strength of the third image remains lower than that of first image 400.

Figure 7A:
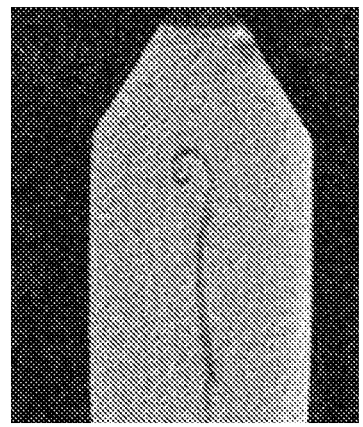
FIGS. 7A and 7B depict MR images of implant devices acquired with low magnetic fields, according to a non-limiting embodiment.
Figure 7B:
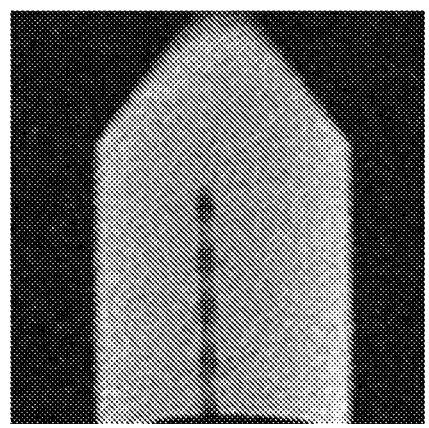

Turning briefly to FIGS. 7A and 7B, examples of second images (obtained at block 310) are shown to illustrate the largely distortion-free characteristics of images captured at reduced magnetic field strengths. FIG. 7A is an MRI scan of a cochlear implant embedded in a uniform gelatin-based medium, and FIG. 7B is an MRI scan of a DBS probe embedded in a similar gelatin-based medium. The images of both FIGS. 7A and 7B were acquired at field strengths of about 0.5 T.

Variations to the above are contemplated. For example, in some embodiments the images obtained at blocks 305 and 310 can be acquired using techniques such as diffusion tensor imaging (DTI), and can thus represent diffusion tracts within patient tissue (e.g. the brain of patient 104). The diffusion tracts (e.g. their orientation, position and dimensions) can be employed at block 315 as features for image registration.

The scope of the claims should not be limited by the embodiments set forth in the above examples, but should be given the broadest interpretation consistent with the description as a whole.

We claim:

1. A method of imaging an implant device in a computing device having a processor interconnected with a memory and a display, comprising, at the processor:
    obtaining a first pre-operative magnetic resonance (MR) image of a patient tissue, the first pre-operative MR image containing a first magnetic field strength indicator;
    after insertion of the implant device in the patient tissue, obtaining a second intra-operative MR image of the patient tissue and the implant device, the second intra-operative MR image containing a second magnetic field strength indicator smaller than the first magnetic field strength indicator;
    registering the second intra-operative MR image with the first pre-operative MR image;
    generating a composite image from the first pre-operative MR image and the second intra-operative MR image, wherein generating the composite image includes:
        for each voxel of the second intra-operative MR image, (i) determining a difference between a value of the voxel and a value of a corresponding voxel of the first pre-operative MR image, (ii) determining whether the difference excedes a threshold and (iii) when the difference exceeds the threshold selecting the voxel of the second intra-operative MR image as indicating a presence of the implant device; and
        substituting the selected voxels of the second intra-operative MR image for the corresponding voxels of the first pre-operative MR image; and
    presenting thee composite image on the display.

2. The method of claim 1, wherein the first pre-operative MR image and the second intra-operative MR image each comprises a quantitative T1 map image.

3. The method of claim 1, wherein the first pre-operative MR image and the second intra-operative MR image each comprises a quantitative T2 map image.

4. The method of claim 1, wherein the first pre-operative MR image and the second intra-operative MR image each comprises a diffusion tensor imaging (DTI) image.

5. The method of claim 1, wherein the implant device comprises one of (i) a deep brain stimulation (DBS) probe and (ii) a cochlear implant.

6. The method of claim 1, further comprising:
obtaining a third MR image of the patient tissue, the third MR image containing a third magnetic field strength indicator smaller than the first magnetic field strength indicator.

7. The method of claim 6, the third magnetic field strength indicator being equal to the second magnetic field strength indicator.

8. The method of claim 6, further comprising:
registering the third MR image with the first pre-operative MR image;
generating a further composite image from the first pre-operative MR image and the third MR image; and
presenting the further composite image on the display in place of the composite image.

9. The method of claim 6, further comprising:
obtaining the third MR image after a positional adjustment of the implant device within the patient tissue.

10. A computing device for imaging an implant device, comprising:
a memory;
a display; and
a processor interconnected with the memory and the display, the processor configured to:
obtain a first pre-operative magnetic resonance (MR) image of a patient tissue, the first pre-operative MR image containing a first magnetic field strength indicator;
after insertion of the implant device in the patient tissue, obtain a second intra-operative MR image of the patient tissue and the implant device, the second intra-operative MR image containing a second magnetic field strength indicator smaller than the first magnetic field strength indicator;
register the second intra-operative MR image with the first pre-operative MR image;
generate a composite image from the first pre-operative MR image and the second intra-operative MR image, wherein generation of the composite image includes:
for each voxel of the second intra-operative MR image: (i) determining a difference between a value of the voxel and a value of a corresponding voxel of the first pre-operative MR image, (ii) determining whether the difference exceeds a threshold, and (iii) when the difference exceeds the threshold, selecting the voxel of the second intra-operative MR image as indicating a presence of the implant device; and
substituting the selected voxels of the second intra-operative MR image for the corresponding voxels of the first pre-operative MR image; and
present the composite image on the display.

11. The computing device of claim 10, wherein the first pre-operative MR image and the second intra-operative MR image each comprises a quantitative T1 map image.

12. The computing device of claim 10, wherein the first pre-operative MR image and the second intra-operative MR image each comprises a quantitative T2 map image.

13. The computing device of claim 10, wherein the first pre-operative MR image and the second intra-operative MR image each comprises a diffusion tensor imaging (DTI) image.

14. The computing device of claim 10, wherein the implant device comprises one of (i) a deep brain stimulation (DBS) probe and (ii) a cochlear implant.

15. The computing device of claim 10, the processor further configured to:
obtain a third MR image of the patient tissue, the third MR image containing a third magnetic field strength indicator smaller than the first magnetic field strength indicator.

16. The computing device of claim 15, the third magnetic field strength indicator being equal to the second magnetic field strength indicator.

17. The computing device of claim 15, the processor further configured to:
register the third MR image with the first pre-operative MR image;
generate a further composite image from the first pre-operative MR image and the third MR image; and
present the further composite image on the display in place of the composite image.

18. The computing device of claim 15, the processor further configured to:
obtain the third MR image after a positional adjustment of the implant device within the patient tissue.

* * * * *